(12) United States Patent
Aoki et al.

(10) Patent No.: US 10,254,241 B2
(45) Date of Patent: Apr. 9, 2019

(54) MULTIPLE GAS DETECTION DEVICE

(71) Applicant: TOYOTA JIDOSHA KABUSHIKI KAISHA, Toyota-shi, Aichi-ken (JP)

(72) Inventors: Keiichiro Aoki, Shizuoka-ken (JP); Koji Ide, Gotenba (JP); Yoshihisa Serizawa, Shizuoka-ken (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 281 days.

(21) Appl. No.: 15/286,964

(22) Filed: Oct. 6, 2016

(65) Prior Publication Data
US 2017/0102354 A1 Apr. 13, 2017

(30) Foreign Application Priority Data

Oct. 8, 2015 (JP) ................. 2015-200113

(51) Int. Cl.
*G01N 27/407* (2006.01)
*G01N 27/406* (2006.01)
(Continued)

(52) U.S. Cl.
CPC ..... *G01N 27/4074* (2013.01); *G01N 27/4067* (2013.01); *G01N 27/417* (2013.01);
(Continued)

(58) Field of Classification Search
CPC .. G01N 27/407; G01N 27/4072; G01N 27/41; G01N 27/409; F01N 2560/00–2560/027
See application file for complete search history.

(56) References Cited

U.S. PATENT DOCUMENTS 3,577,728 A * 5/1971 Von Brimer ............. F01N 3/26
422/182
6,036,841 A 3/2000 Kato et al.
(Continued)

FOREIGN PATENT DOCUMENTS

| JP | H10-38845 A | 2/1998 |
| JP | 2015-034814 A | 2/2015 |
| WO | 2009/108870 A1 | 9/2009 |

*Primary Examiner* — Alexander S Noguerola
(74) *Attorney, Agent, or Firm* — Hunton Andrews Kurth LLP

(57) ABSTRACT

A multiple gas detection device comprises: a first cell part provided with a first electrochemical cell; a second cell part provided with a second electrochemical cell; a third cell part provided with a third electrochemical cell; an inlet diffusion controller controlling diffusion of measured gas; and a measured gas chamber into which the measured gas flows through the inlet diffusion controller. The first cell part is configured to selectively detect a concentration of $NO_x$ or ammonia contained in measured gas in the measured gas chamber. The second cell part is configured to discharge oxygen contained in measured gas in the measured gas chamber and convert $NO_2$ and ammonia contained in measured gas in the measured gas chamber to NO. The third cell part is configured to detect a concentration of NO contained in measured gas in the measured gas chamber.

19 Claims, 3 Drawing Sheets

(51) Int. Cl.
  *G01N 27/417*  (2006.01)
  *G01N 27/419*  (2006.01)
  *G01N 33/00*  (2006.01)

(52) U.S. Cl.
  CPC .. *F01N 2560/021* (2013.01); *F01N 2560/026* (2013.01); *G01N 27/4071* (2013.01); *G01N 27/419* (2013.01); *G01N 33/0037* (2013.01); *G01N 33/0054* (2013.01)

(56) References Cited

U.S. PATENT DOCUMENTS

| | | | |
|---|---|---|---|
| 6,551,497 B1 * | 4/2003 | Gao | G01N 27/4065 204/425 |
| 2002/0043461 A1 * | 4/2002 | Stahl | G01N 27/419 204/425 |
| 2015/0013431 A1 | 1/2015 | Kakimoto et al. | |

* cited by examiner

MULTIPLE GAS DETECTION DEVICE

CROSSED-REFERENCE TO RELATED APPLICATION

The present application claims priority to Japanese Patent Application No. 2015-200113 filed on Oct. 8, 2015, which is incorporated herein by reference in its entirety.

TECHNICAL FIELD

Embodiments of the present invention relate to a multiple gas detection device able to simultaneously detect a plurality of components in a measured gas.

BACKGROUND ART

In recent years, to remove the nitrogen oxides ($NO_x$) contained in the exhaust gas of an internal combustion engine, it has been proposed to provide an $NO_x$ selective reduction catalyst for selectively reducing the $NO_x$ in the exhaust gas inside an exhaust passage of the internal combustion engine. The $NO_x$ selective reduction catalyst adsorbs ammonia and makes the $NO_x$ in inflowing exhaust gas react with the ammonia to reduce and remove the $NO_x$. For example, in such an exhaust purification system, it would be desirable if ammonia and $NO_x$ could be detected.

For this reason, a multiple gas detection device able to detect the concentration of $NO_x$ and the concentration of ammonia contained in measured gas has been proposed (for example, PLT 1). In particular, the multiple gas detection device described in PLT 1 is provided with an $NO_x$ sensor part detecting the concentration of $NO_x$ contained in measured gas and two ammonia sensor parts detecting the concentration of ammonia contained in the measured gas. These two ammonia sensor parts are configured so that the ratios of sensitivity to ammonia and the sensitivity to $NO_x$ differ from each other. According to PLT 1, it is considered that such a configured multiple gas detection device can detect the concentration of $NO_x$ and the concentration of ammonia contained in measured gas.

CITATION LIST

Patent Literature

PLT 1. Japanese Patent Publication No. 2015-34814A
PLT 2. International Publication No. 2009-108870A
PLT 3. Japanese Patent Publication No. 10-038845A

SUMMARY

Technical Problem

In PLT 1, the measured gas detected by the two ammonia cell parts and the measured gas detected by the $NO_x$ sensor part and oxygen concentration detection cell differ. Specifically, the two ammonia sensor parts detect the concentration of, e.g., ammonia in the exhaust gas (measured gas) flowing around the element of the multiple gas detection device, while the $NO_x$ sensor part and oxygen concentration detection cell detect the concentrations of, e.g., $NO_x$ and oxygen in the exhaust gas (measured gas) introduced through the diffusion controller to the measured gas chamber. If, in this way, the ammonia sensor parts and the $NO_x$ sensor part and oxygen concentration detection cell are used to detect the concentrations of components in different measured gas, for example, if a spread of concentration occurs in a specific component in the exhaust gas flowing around the multiple gas detection device, it would not be possible to accurately detect the concentrations of these components.

Therefore, in consideration of the above problem, an object of embodiments of the present invention is to provide a multiple gas detection device able to accurately detect the concentrations of components of a measured gas.

Embodiments of the present invention have been made to solve the above problem, and a summary is as follows.

(1) A multiple gas detection device comprising: a first cell part provided with a first electrochemical cell having a first solid electrolyte having oxide ion conductivity, a first electrode arranged on one side surface of the first solid electrolyte, and a second electrode arranged on the other side surface of the first solid electrolyte; a second cell part provided with a second electrochemical cell having a second solid electrolyte having oxide ion conductivity, a third electrode arranged on one side surface of the second solid electrolyte, and a fourth electrode arranged on the other side surface of the second solid electrolyte; a third cell part provided with a third electrochemical cell having a third solid electrolyte having oxide ion conductivity, a fifth electrode arranged on one side surface of the third solid electrolyte, and a sixth electrode arranged on the other side surface of the third solid electrolyte; an inlet diffusion controller arranged so as to introduce measured gas from outside and controlling diffusion of measured gas passing through it; and a measured gas chamber partitioned and formed by the first solid electrolyte, the second solid electrolyte, the third solid electrolyte, and the inlet diffusion controller, the measured gas chamber having a first measured gas chamber, a second measured gas chamber, and a third measured gas chamber, these first measured gas chamber, second measured gas chamber, and third measured gas chamber being arranged so as to be separated from the inlet diffusion controller in the order of the first measured gas chamber, the second measured gas chamber, and the third measured gas chamber, the first electrode being arranged inside the first measured gas chamber, the third electrode being arranged inside the second measured gas chamber, the fifth electrode being arranged inside the third measured gas chamber, and the second electrode, the fourth electrode, and the sixth electrode being arranged so as to be exposed to a reference gas, wherein the first cell part is configured to selectively detect a concentration of $NO_x$ or ammonia contained in measured gas in the first measured gas chamber, the second cell part is configured to make oxygen contained in measured gas in the second measured gas chamber move from the third electrode to the fourth electrode and convert $NO_2$ and ammonia contained in measured gas in the second measured gas chamber to NO, and the third cell part is configured to detect a concentration of NO contained in measured gas in the third measured gas chamber.

(2) A multiple gas detection device according to above (1), wherein the second cell part is configured to detect a concentration of oxygen in measured gas in the second measured gas chamber in accordance with an amount of movement of oxygen from the third electrode to the fourth electrode.

(3) A multiple gas detection device according to above (1) or (2), wherein the first solid electrolyte, the second solid electrolyte, and the third solid electrolyte are configured as the same single solid electrolyte.

(4) A multiple gas detection device according to any one of above (1) to (3), wherein the second electrode, the fourth electrode, and the sixth electrode are configured as the same single electrode.

(5) A multiple gas detection device according to any one of above (1) to (4), wherein the first cell part is configured to selectively detect a concentration of $NO_x$, and the third cell part is configured to subtract from the concentration of NO contained in measured gas in the third measured gas chamber the concentration of $NO_x$ detected by the first cell part so as to detect a concentration of ammonia contained in measured gas introduced into the measured gas chamber.

(6) A multiple gas detection device according to any one of above (1) to (4), wherein the first cell part is configured to selectively detect a concentration of ammonia, and the third cell part is configured to subtract from the concentration of NO contained in measured gas in the third measured gas chamber the concentration of ammonia detected by the first cell part so as to detect a concentration of $NO_x$ contained in measured gas introduced into the measured gas chamber.

(7) A multiple gas detection device according to any one of above (1) to (6), wherein the third electrode is configured so that its surface area becomes larger than the surface area of the first electrode.

(8) A multiple gas detection device according to any one of above (1) to (7), wherein between the first measured gas chamber and the second measured gas chamber, a first split diffusion controller controlling diffusion of measured gas moving from the first measured gas chamber to the second measured gas chamber is arranged, and between the second measured gas chamber and the third measured gas chamber, a second split diffusion controller controlling diffusion of measured gas moving from the second measured gas.

According to embodiments of the present invention, there is provided a multiple gas detection device able to accurately detect the concentrations of components of a measured gas.

DESCRIPTION OF EMBODIMENTS

Below, embodiments of the present invention will be explained in detail with reference to the drawings. Note that, in the following explanation, similar component elements are assigned the same reference notations.

Figure 1:
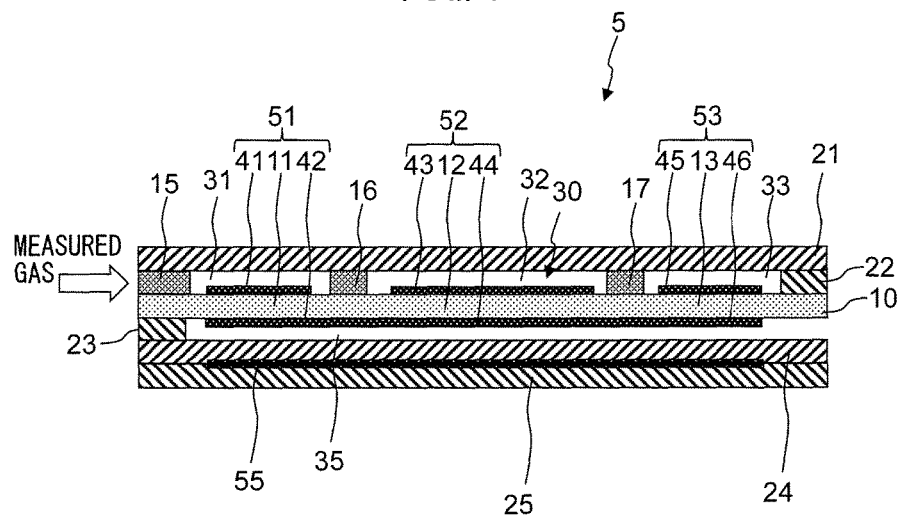
FIG. 1 is a schematic cross-sectional view showing a configuration of an element of a multiple gas detection device according to one embodiment of the present invention.
Figure 2:
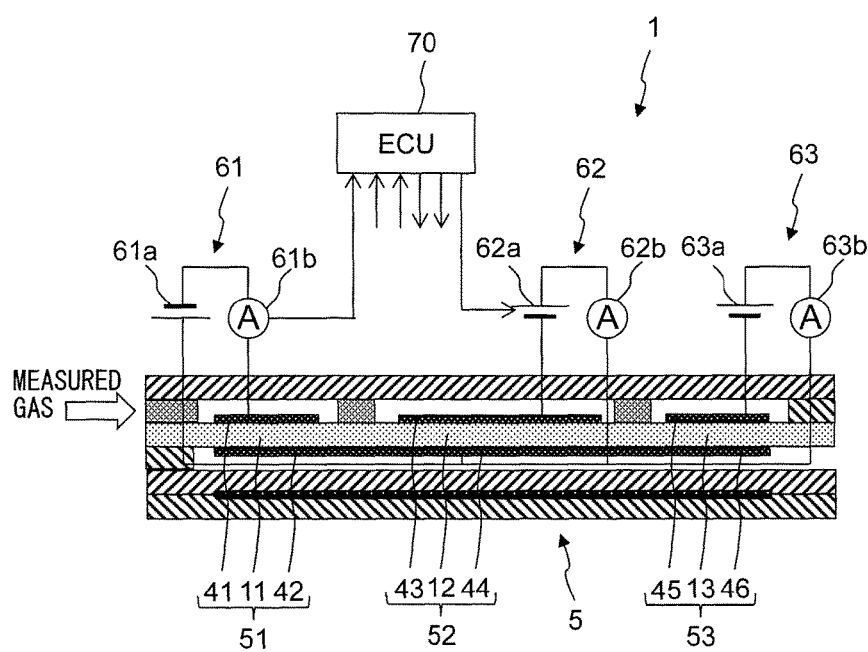
FIG. 2 is a schematic cross-sectional view showing a configuration of a multiple gas detection device according to one embodiment of the present invention.

First, referring to FIG. 1 and FIG. 2, a multiple gas detection device 1 according to one embodiment of the present invention will be explained. FIG. 1 is a schematic cross-sectional view showing a configuration of an element of a multiple gas detection device according to one embodiment of the present invention. Further, FIG. 2 is a schematic cross-sectional view showing a configuration of a multiple gas detection device according to one embodiment of the present invention. The multiple gas detection device 1 is arranged in an exhaust pipe (not shown) of an internal combustion engine and detects the concentrations of the ammonia, $NO_x$, and oxygen contained in the exhaust gas (measured gas) flowing through the exhaust pipe. In particular, in the present embodiment, by detecting the concentration of oxygen contained in the exhaust gas, it is possible to detect the air-fuel ratio of the exhaust gas.

<Configuration of Multiple Gas Detection Device>

The multiple gas detection device 1 according to the present embodiment, as shown in FIG. 1, comprises an element 5 having three electrochemical cells and, as shown in FIG. 2, comprises three circuits 61 to 63 and an electronic control unit (ECU) 70 respectively connected to the three electrochemical cells.

As shown in FIG. 1, the element 5 is configured by a plurality of layers stacked on each other. Specifically, it is provided with a solid electrolyte 10, inlet diffusion controller 15, first split diffusion controller 16, second split diffusion controller 17, first barrier layer 21, second barrier layer 22, third barrier layer 23, fourth barrier layer 24, and fifth barrier layer 25.

The solid electrolyte 10 is a thin sheet member having an oxide ion conductivity. The solid electrolyte 10 is, for example, formed from a sintered body comprised of $ZrO_2$ (zirconia), $HfO_2$, $ThO_2$, and $Bi_2O_3$, in which CaO, MgO, $Y_2O_3$, and $Yb_2O_3$ are blended as stabilizers. In the present embodiment, the solid electrolyte 10 is comprised of three parts. Below, these three parts will be referred to as the first solid electrolyte 11, second solid electrolyte 12, and third solid electrolyte 13.

Further, the inlet diffusion controller 15, first split diffusion controller 16, and second split diffusion controller 17 (below, these being referred to all together as the "diffusion controllers") are thin sheet members having a gas barrier property. The diffusion controllers are, for example, heat resistant inorganic porous sintered bodies made of alumina, magnesia, silicate, spinel, or mullite. The barrier layers 21 to 25 are formed as thin sheet members having a gas barrier property, for example, as layers containing alumina.

The element 5 of the present embodiment is formed from six layers stacked together. From the top in FIG. 1, the first layer is the first barrier layer 21. The second layer has the inlet diffusion controller 15, first split diffusion controller 16, second split diffusion controller 17, and second barrier layer 22. The third layer is the solid electrolyte 10 and is provided with the first solid electrolyte 11, second solid electrolyte 12, and third solid electrolyte 13. The fourth layer is the third barrier layer 23. The fifth layer and the sixth layer are respectively the fourth barrier layer 24 and the fifth barrier layer 25.

The solid electrolyte 10, first barrier layer 21, inlet diffusion controller 15, and second barrier layer 22 partition and form the measured gas chamber 30. The measured gas chamber 30 is configured so that if the multiple gas detection device 1 is arranged in an exhaust pipe, exhaust gas (measured gas) of the internal combustion engine flows into the measured gas chamber 30 through the inlet diffusion controller 15. That is, the multiple gas detection device 1 is arranged in an exhaust pipe so that the inlet diffusion controller 15 is exposed to the exhaust gas. As a result, the measured gas chamber 30 is communicated with the inside of an exhaust passage through the inlet diffusion controller 15. Note that, the measured gas chamber 30 may be configured in any way so long as it is at least partially partitioned and formed by the solid electrolyte 10 and inlet diffusion controller 15.

Further, the measured gas chamber 30 is divided by the first split diffusion controller 16 and second split diffusion controller 17 into the three parts of the first measured gas chamber 31, second measured gas chamber 32, and third measured gas chamber 33. In particular, in the illustrated example, the first measured gas chamber 31, second measured gas chamber 32, and third measured gas chamber 33 are arranged in a direction away from the inlet diffusion controller 15 in the order of the first measured gas chamber 31, second measured gas chamber 32, and third measured gas chamber 33

Note that, between the first measured gas chamber 31 and the second measured gas chamber 32, the first split diffusion controller 16 is arranged for controlling the diffusion of the measured gas moving from the first measured gas chamber 31 to the second measured gas chamber 32. In addition, between the second measured gas chamber 32 and the third measured gas chamber 33, the second split diffusion controller 17 is arranged for controlling the diffusion of the measured gas moving from the second measured gas chamber 32 to the third measured gas chamber 33. However, so long as the measured gas can move between the first measured gas chamber 31 and the second measured gas chamber 32 and between the second measured gas chamber 32 and the third measured gas chamber 33, the diffusion controllers do not necessarily have to be provided. For example, it is also possible to provide a barrier layer provided with small holes running through it between these measured gas chambers or possible to not provide anything.

Further, the solid electrolyte 10, third barrier layer 23, and fourth barrier layer 24 partition and form an atmosphere chamber 35. As will be understood from FIG. 1, the atmosphere chamber 35 is arranged across the solid electrolyte 10 at the opposite side of the measured gas chamber 30. Therefore, the atmosphere chamber 35 is arranged across the first solid electrolyte 11 at the opposite side of the first measured gas chamber 31, is arranged across the second solid electrolyte 12 at the opposite side of the second measured gas chamber 32, and is arranged across the third solid electrolyte 13 at the opposite side of the third measured gas chamber 33. In the present embodiment, the atmosphere chamber 35 is opened to the atmosphere outside of the exhaust pipe. Therefore, atmospheric gas flows into the atmosphere chamber 35. Note that, the atmosphere chamber 35 may be configured in any way so long as it is at least partially partitioned and formed by the solid electrolyte 10. Further, the atmosphere chamber 35 need not necessarily be configured so that atmospheric gas flows into it. For example, it may also be configured so that exhaust gas flows into it. Further, the atmosphere chamber 35 need not necessarily be provided. It is sufficient that one side surface of the solid electrolyte 10 be exposed to the atmosphere or the exhaust gas. Therefore, it can be said that the atmosphere chamber 35 is configured so that a reference gas flows into it and that one side surface of the solid electrolyte 10 is exposed to the reference gas.

Note that, in the present embodiment, the first solid electrolyte 11, second solid electrolyte 12, and third solid electrolyte 13 are formed from a single solid electrolyte 10. However, these first solid electrolyte 11, second solid electrolyte 12, and third solid electrolyte 13 may also be formed as separate solid electrolytes. For example, instead of the first barrier layer 21, a solid electrolyte may be provided. This solid electrolyte may be any of the first solid electrolyte 11, second solid electrolyte 12, and third solid electrolyte 13.

In addition, the element 5 is provided with a first electrode 41, second electrode 42, third electrode 43, fourth electrode 44, fifth electrode 45, and sixth electrode 46. The first electrode 41 is arranged inside the first measured gas chamber 31 and is arranged on the surface of the first solid electrolyte 11 at the first measured gas chamber 31 side. Therefore, the first electrode 41 is exposed to the gas inside the first measured gas chamber 31. The second electrode 42 is arranged inside the atmosphere chamber 35 and is arranged on the surface of the first solid electrolyte 11 at the atmosphere chamber 35 side. Therefore, the second electrode 42 is exposed to the gas inside the atmosphere chamber 35 (atmosphere). Note that, if configured so that exhaust gas flows into the atmosphere chamber 35, the second electrode 42 is exposed to the exhaust gas. The first electrode 41 and the second electrode 42 are arranged so as to face each other across the first solid electrolyte 11. The first electrode 41, first solid electrolyte 11, and second electrode 42 configure a first electrochemical cell 51.

The third electrode 43 is arranged inside the second measured gas chamber 32 and is arranged on the surface of the second solid electrolyte 12 at the second measured gas chamber 32 side. Therefore, the third electrode 43 is exposed to the gas inside the second measured gas chamber 32. On the other hand, the fourth electrode 44 is arranged inside the atmosphere chamber 35 and is arranged on the surface of the second solid electrolyte 12 at the atmosphere chamber 35 side. Therefore, the fourth electrode 44 is exposed to the gas inside the atmosphere chamber 35 (atmosphere). Note that, if configured so that exhaust gas flows into the atmosphere chamber 35, the fourth electrode 44 is exposed to the exhaust gas. The third electrode 43 and the fourth electrode 44 are arranged so as to face each other across the second solid electrolyte 12. The third electrode 43, second solid electrolyte 12, and fourth electrode 44 configure a second electrochemical cell 52.

The fifth electrode 45 is arranged inside the third measured gas chamber 33 and is arranged on the surface of the third solid electrolyte 13 at the third measured gas chamber 33 side. Therefore, the fifth electrode 45 is exposed to the gas inside the third measured gas chamber 33. On the other hand, the sixth electrode 46 is arranged inside the atmosphere chamber 35 and is arranged on the surface of the third solid electrolyte 13 at the atmosphere chamber 35 side. Therefore, the sixth electrode 46 is exposed to the gas inside the atmosphere chamber 35 (atmosphere). Note that, if configured so that exhaust gas flows into the atmosphere chamber 35, the sixth electrode 46 is exposed to the exhaust gas. The fifth electrode 45 and the sixth electrode 46 are arranged so as to face each other across the third solid electrolyte 13. The fifth electrode 45, third solid electrolyte 13, and sixth electrode 46 configure a third electrochemical cell 53.

Note that, in the present embodiment, as shown in FIG. 1, the second electrode 42, fourth electrode 44, and sixth electrode 46 are formed integrally as the same single electrode. Due to this, it is possible to slash the number of parts and possible to reduce the manufacturing costs. However, the second electrode 42, fourth electrode 44, and sixth electrode 46 may also be configured as separate electrodes different from each other.

As explained above, the first measured gas chamber 31, second measured gas chamber 32, and third measured gas chamber 33 are arranged in a direction away from the inlet diffusion controller 15 in the order of the first measured gas chamber 31, second measured gas chamber 32, and third measured gas chamber 33. Therefore, the first electrode 41 arranged inside the first measured gas chamber 31, the third electrode 43 arranged inside the second measured gas chamber 32, and the fifth electrode 45 arranged inside the third measured gas chamber 33 are also arranged in a direction away from the inlet diffusion controller 15 in the order of the first electrode 41, third electrode 43, and fifth electrode 45. Therefore, the measured gas flowing through the inlet diffusion controller 15 into the measured gas chamber 30 first flows around the first electrode 41, next flows around the third electrode 43, and then flows around the fifth electrode 45.

In the present embodiment, the material forming the first electrode 41 includes a lanthanum (La)-based perovskite type oxide as a main component. However, the material forming the first electrode 41 is not necessarily limited to the above material. It may be any material so long as, if applying a predetermined voltage between the first electrode 41 and the second electrode 42, at the first electrode 41, the $NO_x$ contained in the measured gas in the first measured gas chamber 31 can be selectively broken down.

Further, in the present embodiment, the second electrode 42 is a porous cermet electrode having platinum (Pt) as a main component. However, the material forming the second electrode 42 is not necessarily limited to the above material. It may be any material so long as, if applying a predetermined voltage between the first electrode 41 and the second electrode 42, oxide ions can be moved between the first electrode 41 and the second electrode 42.

In addition, in the present embodiment, the third electrode 43 is a porous cermet electrode having, e.g., platinum (Pt) and gold (Au), or alloys of these, as a main component. However, the material forming the third electrode 43 is not necessarily limited to the above materials. It may be any material so long as, if applying a predetermined voltage between the third electrode 43 and the fourth electrode 44, the oxygen contained in the measured gas in the second measured gas chamber 32 can be removed and the $NO_x$ and ammonia contained in the measured gas can be reduced to nitrogen monoxide (NO). Further, in the present embodiment, the fourth electrode 44 is a porous cermet electrode having platinum (Pt) as a main component. In addition, the material forming the fourth electrode 44 is not necessarily limited to the above material. It may be any material so long as, if applying a predetermined voltage between the third electrode 43 and the fourth electrode 43, oxide ions can be moved between the third electrode 43 and the fourth electrode 43.

Further, in the present embodiment, the material forming the fifth electrode 45 contains platinum (Pt) and rhodium (Rh) or other platinum group elements, or alloys of these, as a main component. Preferably the fifth electrode 45 is a porous cermet electrode containing at least one of platinum (Pt), rhodium (Rh), and palladium (Pd) as a main component. However, the material forming the fifth electrode 45 is not necessarily limited to the above materials. It may be any material so long as, if applying a predetermined voltage between the fifth electrode 45 and the sixth electrode 46, the NO contained in the measured gas in the third measured gas chamber 33 can be broken down by reduction.

Further, in the present embodiment, the sixth electrode 46 is a porous cermet electrode having platinum (Pt) as a main component. In addition, the material forming the sixth electrode 46 is not necessarily limited to the above material. It may be any material so long as, if applying a predetermined voltage between the fifth electrode 45 and the sixth electrode 46, oxide ions can be moved between the fifth electrode 45 and the sixth electrode 46. Note that, in the present embodiment, the second electrode 42, fourth electrode 44, and sixth electrode 46 are formed integrally as the same single electrode. Therefore, these second electrode 42, fourth electrode 44, and sixth electrode 46 are formed by the same material.

Note that, the second electrode 42, fourth electrode 44, and sixth electrode 46 do not necessarily have to be integrally formed as a single electrode and may also be formed as separate electrodes. However, if forming these electrodes integrally, it is possible to simplify the manufacturing process and thereby possible to reduce the manufacturing costs.

Further, in the present embodiment, the first electrode 41 and third electrode 43 are configured so that the surface area of the first electrode 41 exposed inside the first measured gas chamber 31 becomes smaller than the surface area of the third electrode 43 exposed inside the second measured gas chamber 32. Further, the third electrode 43 and fifth electrode 45 are configured so that the surface area of the third electrode 43 exposed inside the second measured gas chamber 32 becomes larger than the surface area of the fifth electrode 45 exposed inside the third measured gas chamber 33.

Further, the element part 5 is provided with a heater (electric heater) 55. In the present embodiment, the heater 55, as shown in FIG. 1, is arranged between the fourth barrier layer 24 and the fifth barrier layer 25. The heater 55, for example, is a thin sheet member of cermet containing platinum (Pt) and a ceramic (for example, alumina) and acts as a heat generating member generating heat upon conduction. The heater 55 can heat the first electrochemical cell 51, second electrochemical cell 52, and third electrochemical cell 53 to the activation temperature or more.

As shown in FIG. 2, the first circuit 61 is connected to the first electrode 41 and second electrode 42 of the first electrochemical cell 51 and is provided with a first power supply 61a and a first ammeter 61b. The first power supply 61a and first ammeter 61b are connected to the electronic control unit (ECU) 70. The first power supply 61a supplies voltage between the first electrode 41 and the second electrode 42 so that the potential of the second electrode 42 becomes higher than the potential of the first electrode 41. The magnitude of the voltage supplied by the first power supply 61a is controlled by the ECU 70.

On the other hand, the first ammeter 61b detects the magnitude of the interelectrode current flowing between the first electrode 41 and the second electrode 42 (that is, the current flowing through the first solid electrolyte 11). The value of the interelectrode current detected by the first ammeter 61b is input to the ECU 70.

Further, as shown in FIG. 2, the second circuit 62 is connected to the third electrode 43 and fourth electrode 44 of the second electrochemical cell 52 and is provided with a second power supply 62a and a second ammeter 62b. The second power supply 62a and second ammeter 62b are connected to the ECU 70. The second power supply 62a supplies voltage between the third electrode 43 and fourth electrode 44 so that the potential of the fourth electrode 44 becomes higher than the potential of the third electrode 43. The magnitude of the voltage supplied by the second power supply 62a is controlled by the ECU 70.

On the other hand, the second ammeter 62b detects the magnitude of the interelectrode current flowing between the third electrode 43 and the fourth electrode 44 (that is, the current flowing through the second solid electrolyte 12). The value of the interelectrode current detected by the second ammeter 62*b* is input to the ECU 70.

Further, as shown in FIG. 2, the third circuit 63 is connected to the fifth electrode 45 and sixth electrode 46 of the third electrochemical cell 53 and is provided with a third power supply 63*a* and a third ammeter 63*b*. The third power supply 63*a* and third ammeter 63*b* are connected to the ECU 70. The third power supply 63*a* supplies voltage between the fifth electrode 45 and sixth electrode 46 so that the potential of the sixth electrode 46 becomes higher than the potential of the fifth electrode 45. The magnitude of the voltage supplied by the third power supply 63*a* is controlled by the ECU 70

On the other hand, the third ammeter 63*b* detects the magnitude of the interelectrode current flowing between the fifth electrode 44 and the sixth electrode 46 (that is, the current flowing through the third solid electrolyte 13). The value of the interelectrode current detected by the third ammeter 63*b* is input to the ECU 70.

The ECU 70 is a digital computer comprised of a CPU for performing processing, a ROM for storing a program run by the CPU, and a RAM for temporarily storing data. The ECU is connected to various actuators of an internal combustion engine (e.g., fuel injectors, throttle valves) and controls the operations of these actuators.

The ECU 70 can control the first power supply 61*a* to thereby control the first applied voltage supplied by the first power supply 61*a* between the first electrode 41 and the second electrode 42. Further, the ECU 70 receives as input a signal corresponding to the magnitude of the interelectrode current detected by the first ammeter 61*b* flowing between the first electrode 41 and the second electrode 42. The first electrochemical cell 51, first circuit 61, and ECU 70 configure a first cell part.

Further, the ECU 70 can control the second power supply 62*a* to thereby control the second applied voltage supplied by the second power supply 62*a* between the third electrode 43 and the fourth electrode 44. Further, the ECU 70 receives as input a signal corresponding to the magnitude of the interelectrode current detected by the second ammeter 62*b* flowing between the third electrode 43 and the fourth electrode 44. The second electrochemical cell 52, second circuit 62, and ECU 70 configure a second cell part.

Further, the ECU 70 can control the third power supply 63*a* to thereby control the third applied voltage supplied by the third power supply 63*a* between the fifth electrode 45 and the sixth electrode 46. Further, the ECU 70 receives as input a signal corresponding to the magnitude of the interelectrode current detected by the third ammeter 63*b* flowing between the fifth electrode 45 and the sixth electrode 46. The third electrochemical cell 53, third circuit 63, and ECU 70 configure a third cell part.

<Explanation of Cell Parts>

Next, the first cell part, second cell part, and third cell part of the multiple gas detection device 1 configured as explained above will be specifically explained.

<First Cell Part>

First, the first cell part will be explained. The material forming the first electrode 41 of the first electrochemical cell 51 includes a lanthanum (La)-based perovskite type oxide as its main component. A lanthanum-based perovskite type oxide can selectively adsorb $NO_x$. Therefore, if the first electrode 41 containing the lanthanum-based perovskite type oxide is a main component, if the measured gas in the first measured gas chamber 31 contains $NO_x$, the $NO_x$ is adsorbed at the surface of the first electrode 41.

If, in this state, the first power supply 61*a* of the first cell part supplies voltage between the first electrode 41 and the second electrode 42, the $NO_x$ adsorbed at the electrode is separated into nitrogen and oxide ions. The thus generated oxide ions move through the first solid electrolyte 11 from the first electrode 41 side to the second electrode 42 side, since voltage is supplied using the first electrode 41 as a cathode and the second electrode 42 as an anode.

As the generated oxide ions move, the flow rate of the oxide ions from the first electrode 41 side to the second electrode 42 side changes in accordance with the concentration of $NO_x$ contained in the measured gas. That is, if the concentration of $NO_x$ contained in the measured gas becomes higher, the flow rate of oxide ions moving between the electrodes becomes greater. Conversely, if the concentration of $NO_x$ contained in the measured gas becomes lower, the flow rate of oxide ions moving between the electrodes becomes smaller. The interelectrode current detected by the first ammeter 61*b* of the first cell part is proportional to the flow rate of oxide ions moving between the electrodes.

Figure 3:
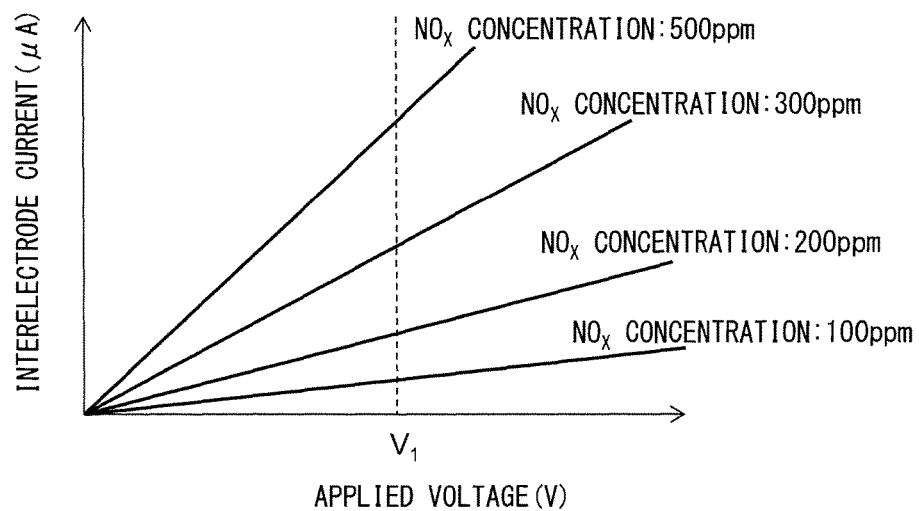
FIG. 3 is a view showing a relationship between an applied voltage and interelectrode current of a first cell part.

FIG. 3 shows the relationship between the applied voltage supplied by the first power supply 61*a* of the first cell part between the first electrode 41 and the second electrode 42, and the interelectrode current detected by the first ammeter 61*b* flowing between these electrodes 41 and 42. In particular, FIG. 3 shows the relationship with respect to four different concentrations of $NO_x$ contained in the measured gas in the first measured gas chamber 31 (100 ppm, 200 ppm, 300 ppm, and 500 ppm).

As will be understood from FIG. 3, at the first cell part, the applied voltage and the interelectrode current are substantially proportional. In addition, as will be understood from FIG. 3, the higher the concentration of $NO_x$ contained in measured gas, the greater the slope. Therefore, if supplying a predetermined first applied voltage $V_1$ between the first electrode 41 and the second electrode 42 of the first electrochemical cell 51, the interelectrode current detected changes in accordance with the concentration of $NO_x$ contained in the measured gas.

Therefore, in the first cell part having the first electrochemical cell 51, by supplying voltage between the first electrode 41 and the second electrode 42 and detecting the interelectrode current flowing between these electrodes 41 and 42, it is possible to detect the concentration of $NO_x$ contained in the measured gas. In particular, at the first electrode 41 containing a lanthanum-based perovskite type oxide as its main component, the oxygen atoms of the $NO_x$ enter the oxygen vacancies, but the oxygen atoms contained in oxygen molecules or water molecules do not enter. Therefore, even if the measured gas has molecules other than $NO_x$ containing oxygen atoms such as oxygen molecules or water molecules, it is de facto possible to selectively detect the concentration of only the $NO_x$ in the measured gas.

Note that, if supplying a voltage of at least a voltage of a certain extent between the first electrode 41 and the second electrode 42 of the first electrochemical cell 51 (for example, 0.60V), the water molecules contained in the measured gas break down on the first electrode 41. As a result, between the first electrode 41 and the second electrode 42, an interelectrode current corresponding to the concentration of water vapor contained in the measured gas flows. For this reason, the precision of detection of the concentration of $NO_x$ contained in the measured gas falls. On the other hand, as will be understood from FIG. 3, the higher the voltage supplied between the first electrode 41 and the second electrode 42 of the first electrochemical cell 51, the greater the extent by which the interelectrode current changes in accordance with the concentration of $NO_x$. Therefore, the voltage supplied between the first electrode 41 and the second electrode 42 of the first electrochemical cell 51 by the first power supply 61a is preferably a voltage of a magnitude as high as possible while less than the voltage of start of breakdown of water. Specifically, the first applied voltage supplied to the first electrochemical cell 51 is made 0.20V to 0.30V.

Further, as explained above, at the first electrode 41 formed by the lanthanum-based perovskite type oxide, the first applied voltage $V_1$ cannot be made too much. Therefore, the speed of breakdown of the $NO_x$ does not become that fast. In addition, as explained above, the first electrode 41 is relatively small in surface area. Therefore, all of the $NO_x$ contained in the measured gas in the first measured gas chamber 31 is not broken down on the first electrode 41. Only a very small part of the $NO_x$ contained in the measured gas is broken down. Therefore, the concentration of $NO_x$ contained in the measured gas flowing from the first measured gas chamber 31 to the second measured gas chamber 32 is almost the same as the concentration of $NO_x$ contained in the measured gas flowing through the inlet diffusion controller 15 into the first measured gas chamber 31.

<Second Cell Part>

Next, the second cell part will be explained. As explained above, the third electrode 43 of the second electrochemical cell 52, is a porous cermet electrode containing, e.g., platinum (Pt) and gold (Au), or alloys of the same, as a main component. Therefore, if supplying voltage between the third electrode 43 at the second measured gas chamber 32 side as the cathode and the fourth electrode 44 as the anode, the oxygen contained in the measured gas in the second measured gas chamber 32 is broken down by reduction resulting in oxide ions.

By voltage being supplied between the third electrode 43 and the fourth electrode 44, the oxide ions move through the second solid electrolyte 12 of the second electrochemical cell 52 from the third electrode 43 to the fourth electrode 44. At the fourth electrode 44, they become oxygen and are discharged to the atmosphere chamber 35. Below, such movement of oxygen due to conduction of oxide ions through the solid electrolyte from the cathode side to the anode side will be called the "oxygen pumping action".

Due to the movement of oxide ions accompanying such an oxygen pumping action, an interelectrode current flows between the third electrode 43 and the fourth electrode 44 configuring the second electrochemical cell 52. This interelectrode current becomes larger the higher the applied voltage supplied between the electrodes 43 and 44 configuring the second electrochemical cell 52. This is because the higher the applied voltage, the greater the amount of movement of oxide ions.

However, if gradually raising the applied voltage to a certain constant value or more, the interelectrode current will not become any larger but will be maintained at a constant value. This characteristic is called a "limit current characteristic of oxygen". A voltage region where the limit current characteristic of oxygen occurs is called a "limit current region of oxygen". Such a limit current characteristic of oxygen occurs due to the speed of movement of oxide ions able to move through the second solid electrolyte 12 along with application of voltage exceeding the speed of introduction of oxygen introduced into the second measured gas chamber 32 through the inlet diffusion controller 15 and first split diffusion controller 16 (if first split diffusion controller 16 is not provided, just inlet diffusion controller 15). That is, it occurs due to the removal of oxygen at the cathode controlling the speed of diffusion.

In this way, if the applied voltage to the second electrochemical cell 52 is made a voltage in the limit current region, the speed of discharge of oxygen from the second measured gas chamber 32 becomes faster than the speed of flow of oxygen into the second measured gas chamber 32. As a result, substantially all of the oxygen is removed from the measured gas inside the second measured gas chamber 32.

Further, in the second electrochemical cell 52, if supplying voltage between the third electrode 43 as the cathode and the fourth electrode 44 as the anode, the $NO_2$ and ammonia contained in the measured gas in the second measured gas chamber 32 are broken down by reduction and become NO. As explained above, the third electrode 43 is large in surface area, so substantially all of the $NO_2$ and ammonia contained in the measured gas in the second measured gas chamber 32 is converted to NO.

Therefore, at the second cell part having the second electrochemical cell 52, by supplying voltage in the limit current region of oxygen between the third electrode 43 and the fourth electrode 44, substantially all of the oxygen can be discharged and removed from the measured gas in the second measured gas chamber 32. In addition, substantially all of the $NO_2$ and ammonia contained in the measured gas in the second measured gas chamber 32 can be converted to NO.

Note that, as explained above, the third electrode 43 is a porous cermet electrode containing, e.g., platinum (Pt) and gold (Au), or an alloy of the same, as a main component. Therefore, the third electrode 43 is inert with respect to the NO on the third electrode 43 or around the third electrode 43. Therefore, even if NO is present on the third electrode 43 or around the third electrode 43, this NO is actually never reduced to nitrogen. Therefore, the $NO_2$ and ammonia in the measured gas in the second measured gas chamber 32 are converted to NO, but the converted NO remains as is without being reduced any further. Therefore, the measured gas moving from the second measured gas chamber 32 to the third measured gas chamber 33 substantially does not contain oxygen, but contains NO.

Further, the interelectrode current if supplying voltage in the limit current region of oxygen in the second electrochemical cell 52 (limit current) corresponds to the concentration of oxygen contained in the measured gas in the second measured gas chamber 32. By utilizing the limit current characteristic of oxygen in this way, it is possible to detect the concentration of oxygen contained in the measured gas inside the second measured gas chamber 32 and use this as the basis to detect the air-fuel ratio of exhaust gas.

Figure 4:
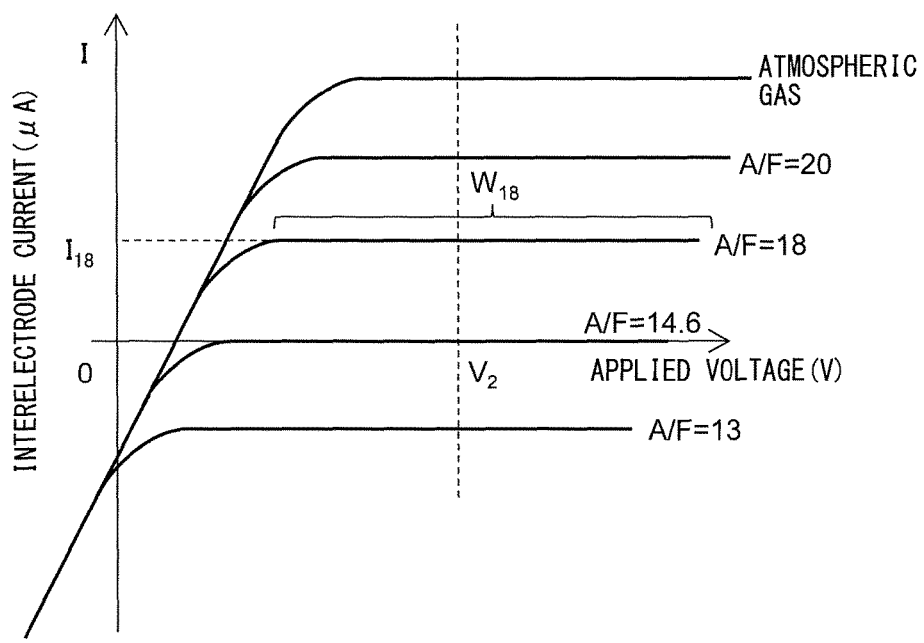
FIG. 4 is a view showing a relationship between an applied voltage and interelectrode current of a second cell part.

FIG. 4 is a view showing a relationship between an applied voltage supplied by the second power supply 62a of the second cell part between the third electrode 43 and the fourth electrode 44, and an interelectrode current detected by the second ammeter 62b flowing between these electrodes 43 and 44. In particular, FIG. 4 shows the relationship if the air-fuel ratio of the measured gas in the second measured gas chamber 32 (corresponding to air-fuel ratio of exhaust gas) is a plurality of different air-fuel ratios (measured gas with air-fuel ratio corresponding to 13.0, 14.6 (stoichiometric air-fuel ratio), 18.0 and 20.0 and atmospheric gas).

As shown in FIG. 4, the interelectrode current becomes larger the higher the air-fuel ratio of the measured gas (that is, the leaner the ratio). Further, the voltage-current curves at different air-fuel ratios of the measured gas have regions parallel to the x-axis, that is, regions where even if the applied voltage changes, the interelectrode current does not change much at all. Such a voltage region is a "limit current region". The current is called a "limit current." In the example shown in FIG. 4, the limit current region and limit current if the air-fuel ratio of the measured gas is 18 are respectively indicated by $W_{18}$ and $I_{18}$.

Therefore, for example, in the example shown in FIG. 4, if supplying the second applied voltage $V_2$ in the limit current region of oxygen between the third electrode 43 and the fourth electrode 44, the interelectrode current changes in accordance with the air-fuel ratio of the measured gas. For this reason, in the present embodiment, by supplying the second applied voltage $V_2$ in the limit current region of oxygen to the second electrochemical cell 52, it is possible to detect the air-fuel ratio of the measured gas.

In this regard, the above-mentioned oxygen pumping action is not an action manifested only with the oxygen contained in the measured gas. Among gases containing oxygen atoms in their molecules, there are other gases where an oxygen pumping action can be manifested. As such a gas, water vapor ($H_2O$) can be mentioned. Therefore, if applying a voltage of at least the voltage where water starts to break down between the third electrode 43 and the fourth electrode 44 of the second electrochemical cell 52, the water vapor contained in the measured gas will break down. The oxide ions generated due to the breakdown of water move from the third electrode 43 to the fourth electrode 44 due to the oxygen pumping action. Along with this, interelectrode current flows between these electrodes. However, if interelectrode current flows due to breakdown of water in this way, it is not possible to accurately detect the air-fuel ratio of the measured gas based on the interelectrode current. For this reason, the voltage supplied by the second power supply 62a to the second electrochemical cell 52 is preferably less than the voltage at which water starts to break down (about 0.60V), for example, is made 0.45V.

<Third Cell Part>

Next, the third cell part will be explained. As explained above, the fifth electrode 45 of the third electrochemical cell 53 is a porous cermet electrode containing at least one of platinum (Pt), rhodium (Rh), and palladium (Pd) as a main component. If using such a configured fifth electrode 45, if supplying voltage between the fifth electrode 45 at the third measured gas chamber 33 side as the cathode and the sixth electrode 46 as the anode, the NO contained in the measured gas in the third measured gas chamber 33 is broken down by reduction. In addition, if supplying voltage between these electrodes, the oxide ions formed by the breakdown of NO move through the third solid electrolyte 13 of the third electrochemical cell 53 from the fifth electrode 45 to the sixth electrode 46. At the sixth electrode 46, they become oxygen and are discharged to the atmosphere chamber 35.

Due to such movement of the oxide ions, interelectrode current flows between the fifth electrode 45 and sixth electrode 46 configuring third electrochemical cell 53. This interelectrode current is proportional to the amount of movement of oxide ions. Further, the amount of movement of oxide ions is proportional to the amount of breakdown of NO on the fifth electrode 45. Therefore, the interelectrode current flowing between the fifth electrode 45 and the sixth electrode 46 is proportional to the concentration of NO in the measured gas in the third measured gas chamber 33. Therefore, based on the interelectrode current at the third electrochemical cell 53 detected by the third ammeter 63b, it is possible to detect the concentration of NO in the measured gas.

Further, the measured gas in the third measured gas chamber 33 flows through the second split diffusion controller 17 from the second measured gas chamber 32. Here, in the second measured gas chamber 32, the second cell part converts the $NO_2$ and ammonia in the measured gas to NO. Therefore, the concentration of NO contained in the measured gas in the third measured gas chamber 33 can be considered to be equal to the total of the concentration of $NO_x$ and the concentration of ammonia contained in the measured gas in the second measured gas chamber 32.

Here, as explained above, at the first cell part, just a very small part of the $NO_x$ in the measured gas in the first measured gas chamber 31 is broken down. Therefore, the concentration of $NO_x$ contained in the measured gas flowing from the first measured gas chamber 31 to the second measured gas chamber 32 is almost the same as the concentration of $NO_x$ contained in the measured gas flowing through the inlet diffusion controller 15 into the first measured gas chamber 31. Therefore, the concentration of NO contained in the measured gas in the third measured gas chamber 33 can be considered to be the total of the concentration of $NO_x$ and the concentration of ammonia contained in the measured gas flowing through the inlet diffusion controller 15 into the measured gas chamber 30. Therefore, at the third cell part, by calculating the concentration of NO contained in the measured gas in the third measured gas chamber 33, it is possible to calculate the total of the concentration of $NO_x$ and the concentration of ammonia contained in the measured gas flowing through the inlet diffusion controller 15 into the measured gas chamber 30.

Figure 5:
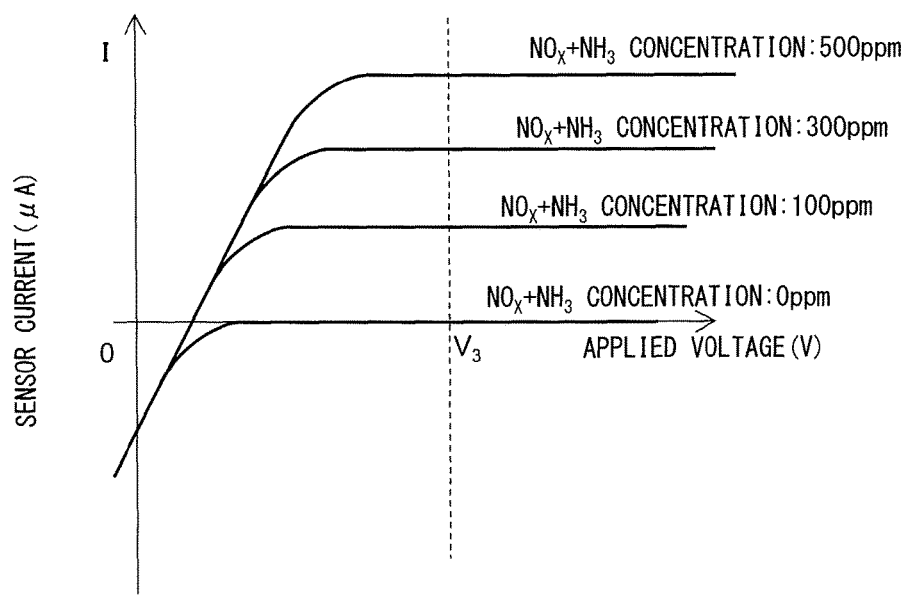
FIG. 5 is a view showing a relationship between an applied voltage and interelectrode current of a third cell part.

FIG. 5 is a view showing a relationship between an applied voltage supplied by the third power supply 63a of the third cell part between the fifth electrode 45 and the sixth electrode 46, and the interelectrode current detected by the third ammeter 63b flowing between these electrodes 45 and 46. In particular, FIG. 5 shows the relationship if the total of the concentration of $NO_x$ and concentration of ammonia of measured gas in the third measured gas chamber 33 (below, "total concentration") is a plurality of different concentrations (0 ppm, 100 ppm, 300 ppm, and 500 ppm).

As shown in FIG. 5, the interelectrode current becomes larger the higher the total concentration. Further, the voltage-current curves at the different total concentrations of $NO_x$ and ammonia in the measured gas include regions parallel to the x-axis, that is, regions where even if the applied voltage changes, the interelectrode current does not change much at all. Such a voltage region is a "limit current region of NO". The current is a limit current. Therefore, for example, in the example shown in FIG. 5, by supplying the third applied voltage $V_3$ within the region of the limit current of NO between the fifth electrode 45 and the sixth electrode 46, the interelectrode current changes in accordance with the total concentration of $NO_x$ and ammonia of the measured gas. For this reason, in the present embodiment, by supplying the third applied voltage $V_3$ within the region of the limit current of NO to the third electrochemical cell 53, the total concentration of $NO_x$ and ammonia can be detected.

<Operation of Multiple Gas Detection Device>

Figure 6:
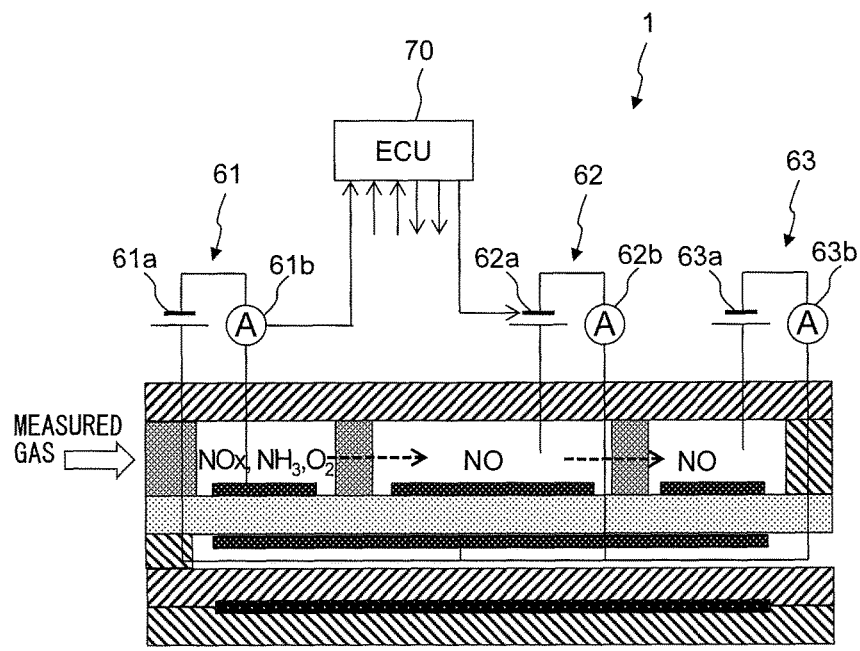
FIG. 6 is a cross-sectional view, similar to FIG. 1 and FIG. 2, schematically showing the flow of measured gas.

Next, referring to FIG. 6, a detection operation by the multiple gas detection device 1 configured as explained above will be explained in detail. FIG. 6 is a cross-sectional view, similar to FIG. 1 and FIG. 2, schematically showing the flow of the measured gas.

As shown in FIG. 6, the inlet diffusion controller 15 of the multiple gas detection device 1 is exposed to the exhaust gas being measured (measured gas). Therefore, first, the measured gas flows into the first measured gas chamber 31. The measured gas flowing into the first measured gas chamber 31 contains oxygen, $NO_x$, and ammonia.

At the first measured gas chamber 31, the first electrode 41 of the first electrochemical cell 51 of the first cell part is arranged. For this reason, if the first applied voltage $V_1$ is supplied to the first electrochemical cell 51 by the first power supply 61a, as explained above, the $NO_x$ contained in the measured gas in the first measured gas chamber 31 will be selectively broken down. Along with the selective breakdown of this $NO_x$, an interelectrode current proportional to the concentration of $NO_x$ contained in the measured gas in the first measured gas chamber 31 will flow between the first electrode 41 and the second electrode 42. Therefore, based on the interelectrode current flowing between the first electrode 41 and the second electrode 42 detected by the first ammeter 61b, it is possible to detect the concentration of $NO_x$.

After that, the measured gas in the first measured gas chamber 31 flows through the first split diffusion controller 16 to the second measured gas chamber 32. The first cell part only breaks down the $NO_x$ a little, so the components of the measured gas flowing from the first measured gas chamber 31 to the second measured gas chamber 32 basically are the same as the components of the measured gas flowing through the inlet diffusion controller 15 to the first measured gas chamber 31. Therefore, the measured gas flowing into the second measured gas chamber 32 contains oxygen, $NO_x$, and ammonia.

At the second measured gas chamber 32, the third electrode 43 of the second electrochemical cell 52 of the second cell part is arranged. For this reason, if the second applied voltage $V_2$ is supplied to the second electrochemical cell 52 by the second power supply 62a, as explained above, the oxygen contained in the measured gas in the second measured gas chamber 32 will be discharged to the atmosphere chamber 35. In particular, in the present embodiment, along with the discharge of oxygen, the oxygen concentration or air-fuel ratio of the measured gas in the second measured gas chamber 32 (corresponding to air-fuel ratio of exhaust gas) is detected by the second ammeter 62b. Further, at the second measured gas chamber 32, if the second applied voltage $V_2$ is applied to the second electrochemical cell 52 by the second power supply 62a, the $NO_2$ and ammonia contained in the measured gas are converted to NO on the third electrode 43, but NO is not broken down on the third electrode 43.

After that, the measured gas in the second measured gas chamber 32 flows through the second split diffusion controller 17 into the third measured gas chamber 33. Inside the second measured gas chamber 32, oxygen is removed from the measured gas and the $NO_2$ and ammonia in the measured gas are converted to NO, so the measured gas flowing into the third measured gas chamber 33 contains NO, but does not contain oxygen, $NO_2$, and ammonia.

At the third measured gas chamber 33, a fifth electrode 45 of the third electrochemical cell 53 of the third cell part is arranged. For this reason, if the third applied voltage $V_3$ is supplied by the third power supply 63a to the third electrochemical cell 53, as explained above, the NO contained in the measured gas in the third measured gas chamber 33 is broken down on the fifth electrode 45. Along with the breakdown of NO, an interelectrode current proportional to the concentration of NO contained in the measured gas in the measured gas chamber 33 flows between the fifth electrode 45 and the sixth electrode 46. Therefore, it is possible to detect the concentration of NO based on the interelectrode current flowing between the fifth electrode 45 and sixth electrode 46 detected by the third ammeter 63b.

In addition, the detected concentration of NO, as explained above, expresses the total concentration of the concentration of $NO_x$ and the concentration of ammonia contained in the measured gas flowing from the outside to the inside of the measured gas chamber 30. As opposed to this, the concentration of $NO_x$ contained in the measured gas flowing from the outside to the inside of the measured gas chamber 30 is already detected based on the output of the first ammeter 61b. Therefore, the third cell part subtracts from the total concentration of the concentration of $NO_x$ and the concentration of ammonia (concentration of NO detected by third cell part) the concentration of $NO_x$ contained in the measured gas flowing from the outside to the inside of the measured gas chamber 30 (concentration of $NO_x$ detected by first cell part) to calculate the concentration of ammonia.

Specifically, the concentration of ammonia is for example calculated as follows. First, the ECU 70 configuring the first cell part calculates the concentration of $NO_x$ based on the interelectrode current of the first electrochemical cell 51, using a map showing a relationship between the interelectrode current and concentration of $NO_x$ found in advance. In addition, the ECU 70 configuring the third cell part calculates the total concentration of $NO_x$ and ammonia based on the interelectrode current of the third electrochemical cell 53 of the third cell part, using a map showing a relationship between the interelectrode current and the total concentration of $NO_x$ and ammonia found in advance. After that, the ECU 70 configuring the third cell part subtracts from the total concentration detected at the third cell part the concentration of $NO_x$ calculated at the ECU 70 forming part of the first cell part so as to calculate the concentration of ammonia.

Note that, the concentration of ammonia does not actually have to be calculated by the specific technique such as explained above. For example, it is also possible to subtract from the value of the interelectrode current of the third electrochemical cell 53 the value of the interelectrode current of the first electrochemical cell 51 multiplied with a predetermined coefficient and to calculate the concentration of ammonia based on the value found by subtraction, e.g., using a map.

<Advantageous Effects>

Next, the effects of the multiple gas detection device having the above-mentioned configuration and operating as explained above will be explained.

In the multiple gas detection device of the present embodiment, the first cell part, second cell part, and third cell part for detecting the concentrations of the various components all detect the concentrations of various components of the measured gas flowing through the inlet diffusion controller 15 to the measured gas chamber 30. Therefore, the first cell part, second cell part, and third cell part perform detection on the same measured gas.

In this regard, if these cell parts detect different measured gases or these cell parts perform detection at different timings, sometimes the components in the measured gases being detected will end up differing at each cell part. As opposed to this, according to the multiple gas detection device of the present embodiment, the first cell part, second cell part, and third cell part can perform detection for the same measured gas, so it becomes possible to accurately detect the concentrations of the various components in the measured gas.

Further, as explained above, in detecting the concentration of a specific component in measured gas, it may be considered to detect the concentration of the specific component based on the electromotive force generated across electrodes of an electrochemical cell. However, detection of the concentration of a specific component based on such electromotive force is relatively low in precision and slow in speed of response. As opposed to this, in the present embodiment, each of the first electrochemical cell 51, second electrochemical cell 52, and third electrochemical cell 53 detects the concentration of a specific component by passing current between electrodes. Therefore, in the present embodiment, it is possible to detect the concentrations of specific components by a high precision and with a fast response.

In addition, in the above embodiments, the first split diffusion controller is provided between the first measured gas chamber 31 and the second measured gas chamber 32, while the second split diffusion controller is provided between the second measured gas chamber 32 and the third measured gas chamber 33. Therefore, the free flow of measured gas between the first measured gas chamber 31 and second measured gas chamber 32 and between the second measured gas chamber 32 and third measured gas chamber 33 is restricted. As a result, it is possible to raise the detection precisions at the electrochemical cells 51, 52, and 53.

Other Embodiments

Note that, in the above embodiment, the first cell part is configured to be able to selectively break down the $NO_x$ contained in the measured gas in the first measured gas chamber 31 and along with this selectively detect the concentration of $NO_x$ in the measured gas. However, the first cell part may also be configured to be able to selectively break down the ammonia contained in the measured gas in the first measured gas chamber 31 and along with this selectively detect the concentration of ammonia in the measured gas. Specifically, in this example, as the first electrochemical cell 51, an amperometric ceramic chemical cell is used. Further, in this example, the third cell part subtracts from the total concentration of the concentration of $NO_x$ and the concentration of ammonia detected by the third cell part (concentration of NO detected by third cell part) the concentration of ammonia contained in measured gas flowing from the outside into the measured gas chamber 30 (concentration of ammonia detected by first cell part) to thereby calculate the concentration of $NO_x$.

What is claimed is:

1. A multiple gas detection device comprising
a first cell part provided with a first electrochemical cell having a first solid electrolyte having oxide ion conductivity, a first electrode arranged on one side surface of the first solid electrolyte, and a second electrode arranged on the other side surface of the first solid electrolyte,
a second cell part provided with a second electrochemical cell having a second solid electrolyte having oxide ion conductivity, a third electrode arranged on one side surface of the second solid electrolyte, and a fourth electrode arranged on the other side surface of the second solid electrolyte,
a third cell part provided with a third electrochemical cell having a third solid electrolyte having oxide ion conductivity, a fifth electrode arranged on one side surface of the third solid electrolyte, and a sixth electrode arranged on the other side surface of the third solid electrolyte,
an inlet diffusion controller arranged so as to introduce measured gas from outside and controlling diffusion of measured gas passing through it, and
a measured gas chamber partitioned and formed by the first solid electrolyte, the second solid electrolyte, the third solid electrolyte, and the inlet diffusion controller,
the measured gas chamber having a first measured gas chamber, a second measured gas chamber, and a third measured gas chamber, the first measured gas chamber, second measured gas chamber, and third measured gas chamber being arranged so as to be separated from the inlet diffusion controller in the order of the first measured gas chamber, the second measured gas chamber, and the third measured gas chamber,
the first electrode being arranged inside the first measured gas chamber, the third electrode being arranged inside the second measured gas chamber, the fifth electrode being arranged inside the third measured gas chamber, and the second electrode, the fourth electrode, and the sixth electrode being arranged so as to be exposed to a reference gas, wherein
the first cell part is configured to selectively detect a concentration of $NO_x$ or ammonia contained in measured gas in the first measured gas chamber,
the second cell part is configured to make oxygen contained in measured gas in the second measured gas chamber move from the third electrode to the fourth electrode and convert $NO_2$ and ammonia contained in measured gas in the second measured gas chamber to NO, and
the third cell part is configured to detect a concentration of NO contained in measured gas in the third measured gas chamber.

2. The multiple gas detection device according to claim 1, wherein the second cell part is configured to detect a concentration of oxygen in measured gas in the second measured gas chamber in accordance with an amount of movement of oxygen from the third electrode to the fourth electrode.

3. The multiple gas detection device according to claim 2, wherein the first solid electrolyte, the second solid electrolyte, and the third solid electrolyte are configured as the same single solid electrolyte.

4. The multiple gas detection device according to claim 3, wherein the second electrode, the fourth electrode, and the sixth electrode are configured as the same single electrode.

5. The multiple gas detection device according to claim 4, further comprising an electronic control unit (ECU), wherein
the first cell part is configured to selectively detect the concentration of $NO_x$,
the second cell part is configured to flow NO into the third cell part,
the third cell part is configured to detect the concentration of NO in measured gas in the third measured gas chamber, and
the ECU is configured to detect a concentration of ammonia contained in measured gas introduced into the gas chamber by subtracting the concentration of $NO_x$ detected by the first cell part from the concentration of NO detected by the third cell part.

6. The multiple gas detection device according to claim 3, further comprising an electronic control unit (ECU), wherein
the first cell part is configured to selectively detect the concentration of $NO_x$, the second cell part is configured to flow NO into the third cell part, the third cell part is configured to detect the concentration of NO in measured gas in the third measured gas chamber, and the ECU is configured to detect a concentration of ammonia contained in measured gas introduced into the gas chamber b subtracting the concentration of $NO_x$ detected by the first cell part from the concentration of NO detected by the third cell part.

7. The multiple gas detection device according to claim 2, wherein the second electrode, the fourth electrode, and the sixth electrode are configured as the same single electrode.

8. The multiple gas detection device according to claim 7, further comprising an electronic control unit (ECU), wherein the first cell part is configured to selectively detect the concentration of $NO_x$, the second cell part is configured to flow NO into the third cell part, the third cell part is configured to detect the concentration of NO in measured gas in the third measured gas chamber, and the ECU is configured to detect a concentration of ammonia contained in measured vas introduced into the gas chamber by subtracting the concentration of $NO_x$ detected by the first cell part from the concentration of NO detected by the third cell part.

9. The multiple gas detection device according to claim 2, further comprising an electronic control unit (ECU), wherein the first cell part is configured to selectively detect the concentration of $NO_x$, the second cell part is configured to flow NO into the third cell part, the third cell part is configured to detect the concentration of NO n measured gas in the third measured gas chamber, and the ECU is configured to detect a concentration of ammonia contained in measured gas introduced into the gas chamber by subtracting the concentration of $NO_x$ detected by the first cell part from the concentration of NO detected by the third cell part.

10. The multiple gas detection device according to claim 1, wherein the first solid electrolyte, the second solid electrolyte, and the third solid electrolyte are configured as the same single solid electrolyte.

11. The multiple gas detection device according to claim 10, wherein the second electrode, the fourth electrode, and the sixth electrode are configured as the same single electrode.

12. The multiple gas detection device according to claim 11, further comprising an electronic control unit (ECU), wherein the first cell part is configured to selectively detect the concentration of $NO_x$, the second cell part is configured to flow NO into the third cell part, the third cell part is configured to detect the concentration of NO in measured gas in the third measured gas chamber, and the ECU is configured to detect a concentration of ammonia contained in measured gas introduced into the gas chamber by subtracting the concentration of $NO_x$ detected by the first cell part from the concentration of NO detected by the third cell part.

13. The multiple gas detection device according to claim 10, further comprising an electronic control unit (ECU), wherein the first cell part is configured to selectively detect the concentration of $NO_x$, the second cell part is configured to flow NO into the third cell part, the third cell part is configured to detect the concentration of NO in measured gas in the third measured gas chamber, and the ECU is configured to detect a concentration of ammonia contained in measured gas introduced into the gas chamber by subtracting the concentration of $NO_x$ detected by the first cell part from the concentration of NO detected by the third cell part.

14. The multiple gas detection device according to claim 1, wherein the second electrode, the fourth electrode, and the sixth electrode are configured as the same single electrode.

15. The multiple gas detection device according to claim 14, further comprising an electronic control unit (ECU), wherein the first cell part is configured to selectively detect the concentration of $NO_x$, the second cell part is configured to flow NO into the third cell part, the third cell part is configured to detect the concentration of NO in measured gas in the third measured gas chamber, and the ECU is configured to detect a concentration of ammonia contained in measured gas introduced into the gas chamber by subtracting the concentration of $NO_x$ detected by the first cell part from the concentration of NO detected by the third cell part.

16. The multiple gas detection device according to claim 1, further comprising an electronic control unit (ECU), wherein the first cell part is configured to selectively detect the concentration of $NO_x$, the second cell part is configured to flow NO into the third cell part, the third cell part is configured to detect the concentration of NO in measured gas in the third measured gas chamber, and the ECU is configured to detect a concentration of ammonia contained in measured gas introduced into the gas chamber by subtracting the concentration of $NO_x$ detected by the first cell part from the concentration of NO detected by the third cell part.

17. The multiple gas detection device according to claim 1, further comprising an electronic control unit (ECU), wherein the first cell part is configured to selectively detect the concentration of ammonia, the second cell part is configured to flow NO into the third cell part, the third cell part is configured to detect the concentration of NO in measured gas in the third measured gas chamber, and the ECU is configured to detect a concentration of $NO_x$ contained in measured gas introduced into the gas chamber by subtracting the concentration of ammonia detected by the first cell part from the concentration of NO detect by the third cell part.

18. The multiple gas detection device according to claim 1, wherein the third electrode is formed so that a surface area of the third electrode is larger than a surface area of the first electrode.

19. The multiple gas detection device according to claim 1, wherein
  between the first measured gas chamber and the second measured gas chamber, a first split diffusion controller is arranged to control diffusion of the measured gas moving from the first measured gas chamber to the second measured gas chamber, and
  between the second measured gas chamber and the third measured gas chamber, a second split diffusion controller is arranged to control diffusion of the measured gas moving from the second measured gas chamber to the third measured gas chamber.

* * * * *